United States Patent
Silverman et al.

(10) Patent No.: US 10,618,926 B2
(45) Date of Patent: Apr. 14, 2020

(54) PROCESS FOR MAKING PHOSPHORAMIDATE PROTECTED NUCLEOSIDE COMPOUNDS

(71) Applicants: Steven M. Silverman, Jersey City, NJ (US); Bryon Ladd Simmons, Hamilton, NJ (US); Zhuqing Liu, Edison, NJ (US); Jing Liao, Livingston, NJ (US); Artis Klapars, Edison, NJ (US); Kevin R. Campos, Berkeley Heights, NJ (US); Ana Inés Bellomo Peraza, Ciudad de Buenos Aires (AR); MERCK SHARP & DOHME CORP., Rahway, NJ (US)

(72) Inventors: Steven M. Silverman, Jersey City, NJ (US); Bryon Ladd Simmons, Hamilton, NJ (US); Zhuqing Liu, Edison, NJ (US); Jing Liao, Livingston, NJ (US); Artis Klapars, Edison, NJ (US); Kevin R. Campos, Berkeley Heights, NJ (US); Ana Inés Bellomo Peraza, Ciudad de Buenos Aires (AR)

(73) Assignee: Merck Sharp & Dohme, Rahway, NJ (US)

(*) Notice: Subject to any disclaimer, the term of this patent is extended or adjusted under 35 U.S.C. 154(b) by 0 days.

(21) Appl. No.: 15/562,973

(22) PCT Filed: Mar. 28, 2016

(86) PCT No.: PCT/US2016/024411
§ 371 (c)(1),
(2) Date: Sep. 29, 2017

(87) PCT Pub. No.: WO2016/160646
PCT Pub. Date: Oct. 6, 2016

(65) Prior Publication Data
US 2018/0111954 A1  Apr. 26, 2018

Related U.S. Application Data

(60) Provisional application No. 62/142,252, filed on Apr. 2, 2015.

(51) Int. Cl.
| | |
|---|---|
| C07H 1/02 | (2006.01) |
| C07F 9/58 | (2006.01) |
| C07F 9/6558 | (2006.01) |
| C07H 19/10 | (2006.01) |
| C07H 19/20 | (2006.01) |
| C07F 9/24 | (2006.01) |

(52) U.S. Cl.
CPC ............ C07H 1/02 (2013.01); C07F 9/242 (2013.01); C07F 9/58 (2013.01); C07F 9/65586 (2013.01); C07H 19/10 (2013.01); C07H 19/20 (2013.01)

(58) Field of Classification Search
CPC ..... C07F 9/572; C07F 9/6521; C07F 9/65324
See application file for complete search history.

(56) References Cited

U.S. PATENT DOCUMENTS

| | | | |
|---|---|---|---|
| 7,879,815 B2 | 2/2011 | MacCoss et al. | |
| 10,251,903 B2* | 4/2019 | Simmons | ............... C07H 19/10 |
| 2004/0023987 A1 | 2/2004 | Hata et al. | |
| 2010/0234316 A1 | 9/2010 | MacCoss et al. | |
| 2013/0281686 A1 | 10/2013 | Cho et al. | |
| 2014/0121366 A1 | 5/2014 | Chun et al. | |
| 2017/0218006 A1* | 8/2017 | Wilhelm | ............... C07H 19/06 |

FOREIGN PATENT DOCUMENTS

| | | | | |
|---|---|---|---|---|
| EP | 14179385.1 | * | 7/2014 | ............ C07H 19/10 |
| WO | 1992007864 A1 | | 5/1992 | |
| WO | WO2005003147 | | 1/2005 | |
| WO | WO2009132123 | | 10/2009 | |
| WO | 20100002877 | | 1/2010 | |
| WO | 2010075517 | | 7/2010 | |
| WO | 2010081628 | | 7/2010 | |
| WO | 2011035231 | | 3/2011 | |
| WO | WO2013177219 A1 | | 11/2013 | |
| WO | WO2014058801 A1 | | 4/2014 | |
| WO | 2015034420 A1 | | 3/2015 | |

OTHER PUBLICATIONS

International Search Report and Written Opinion for PCT/US2016/024411, dated Jun. 30, 2016; 8 pages.

* cited by examiner

*Primary Examiner* — Pancham Bakshi

(74) *Attorney, Agent, or Firm* — Jeffrey P. Bergman; Catherine D. Fitch

(57) ABSTRACT

The present invention is directed to process for making Compounds of Formula (II): (II), and salts thereof, wherein B, X, $R^2$, $R^3$, $R^4$ $R^7$, $R^8$ and $R^9$ are defined herein.

(II)

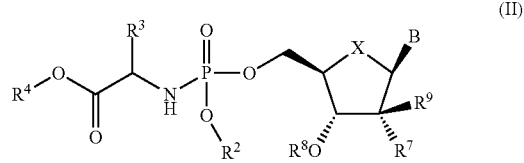

10 Claims, No Drawings

PROCESS FOR MAKING PHOSPHORAMIDATE PROTECTED NUCLEOSIDE COMPOUNDS

CROSS-REFERENCE TO RELATED APPLICATIONS

This application is the national stage application under 35 U.S.C. 371 of International Patent Application No. PCT/US2016/024411, filed Mar. 28, 2016, which claims priority to U.S. Provisional Patent Application No. 62/142,252, filed Apr. 2, 2015. Each of the aforementioned applications is incorporated by reference in its entirety.

FIELD OF THE INVENTION

The present invention is directed to a process for making Nucleoside Phosphoramidate Compounds which may be useful for the treatment or prophylaxis of HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, and is estimated to affect approximately 2-15% of the world's population. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, sexually or vertically from infected mothers or carrier mothers to their off-spring.

Inhibition of HCV NS5B polymerase prevents formation of the double-stranded HCV RNA and therefore constitutes an attractive approach to the development of HCV-specific antiviral therapies.

Various substituted nucleoside compounds are known inhibitors of the HCV NS5B protease enzyme. Included in these nucleosides are nucleoside phosphoramidate compounds which may be useful in the treatment of infection by HCV and in the treatment, prophylaxis, or delay in the onset or progression of HCV infection. Representative nucleoside phosphoramidate compounds that may be useful for treating HCV infection are described, for example, in International Patent Publication Nos. WO 2013/177219 and WO 2014/058801.

The development of inhibitors of HCV NS5B polymerase with potential for the treatment of HCV infection has been reviewed in Poorad et al., *J. Viral. Hepat.* 19(7): 449-464 (2012); Asselah et al., *Liver Int.,* 29 Suppl 1: 57-67(2009); and Chatel-Chaix et al. *Current Opinion in Virology,* 2:588-598 (2012). Nucleoside analogs that inhibit HCV NS5B polymerase are disclosed, for example, in WO 2011/035231, WO 2005/003147, WO 2010/0081628, U.S. Pat. No. 7,879,815, WO 2010/075517, WO 2010/002877, and WO 2009/132123.

Among these nucleoside analogs are prodrugs which have the 5'-OH group masked as a phosphoramidate moiety (also referred to as "McGuigan" prodrugs). See, for example, Bobeck et al., *Antiviral Therapy,* 15: 935-950 (2010); and McGuigan et al., *Bioorg Med Chem Lett,* 20(16):4850-4854 (2010). U.S. Pat. No. 8,629,263 discloses reagents that can be used to add phosphoramidate groups onto nucleoside compounds to prepare McGuigan type prodrugs.

SUMMARY OF THE INVENTION

The present invention is directed to a process for making Nucleoside Phosphoramidate Compounds of Formula (II) which may be useful for the treatment and prophylaxis of HCV infection. More particularly, the present invention includes a process (alternatively referred to herein as "Process A") for preparing a compound of Formula (II):

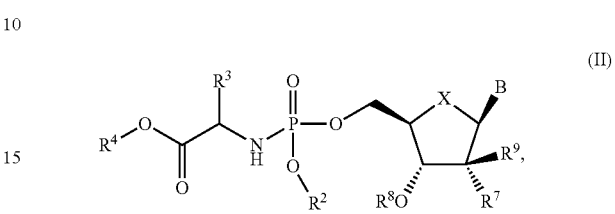

said process comprising the step of contacting a compound of formula (I):

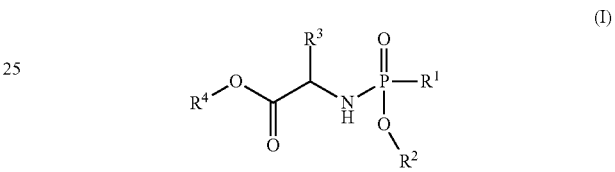

with a compound of formula (III):

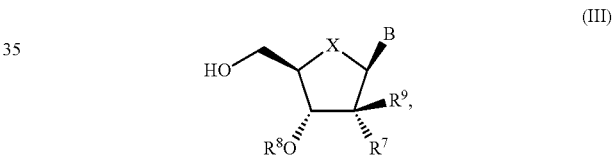

in the presence of an aluminum complex and a non-nucleophilic base, in an organic solvent A for a time and at a temperature sufficient to form the compound of formula (II), wherein:
X is O, S or $CH_2$;
B is a natural or non-natural purine or pyrimidine base, or B is selected from one of the following groups:

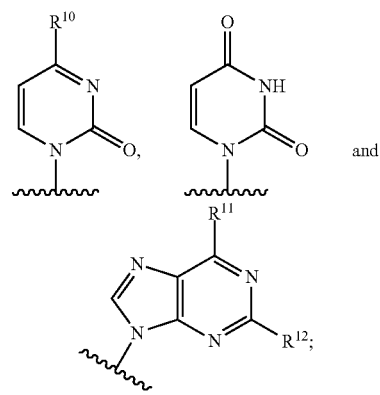

$R^1$ is selected from —O—($C_6$-$C_{10}$ aryl), 5 or 6-membered monocyclic heteroaryl, 9 or 10-membered bicyclic heteroaryl, —O-(5 or 6-membered monocyclic heteroaryl), —O-(9 or 10-membered bicyclic heteroaryl), —O-(4 to 7-membered monocyclic heterocycloalkyl), —S-(5 or 6-membered monocyclic heteroaryl), —S-(9 or 10-membered bicyclic heteroaryl), —S-(4 to 7-membered monocyclic heterocycloalkyl) or 10-membered heteroaryl) and —S—($C_6$-$C_{10}$ aryl), wherein any of said 5 or 6-membered monocyclic heteroaryl groups, any of said 9 or 10-membered bicyclic heteroaryl groups, any of said 4 to 7-membered monocyclic heterocycloalkyl groups, and any of said $C_6$-$C_{10}$ aryl groups can each be optionally substituted with one or more $R^5$ groups;

$R^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more $R^5$ groups;

$R^3$ is selected from $C_1$-$C_6$ alkyl, $C_3$-$C_7$ cycloalkyl, phenyl or benzyl, wherein said $C_3$-$C_7$ cycloalkyl group, said phenyl group and the phenyl moiety of said benzyl group can be optionally substituted with one or more $R^5$ groups;

$R^4$ is selected from $C_1$-$C_6$ alkyl, $C_2$-$C_6$ alkenyl, —($C_1$-$C_3$ alkylene)$_m$-($C_3$-$C_{14}$ cycloalkyl) and —($C_1$-$C_3$ alkylene)$_m$-($C_6$-$C_{10}$ aryl);

each occurrence of $R^5$ is independently selected from —$C_1$-$C_6$ alkyl, halo, —$OR^6$, —$C(O)R^6$, —$C(O)OR^6$, —$SR^6$, —$C_1$-$C_6$ hydroxyalkyl, —$C_1$-$C_6$ haloalkyl, —$N(R^6)_2$, —$S(O)R^6$, —$S(O)_2R^6$, —CN and —$NO_2$;

each occurrence of $R^6$ is independently H, $C_1$-$C_6$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

$R^7$ is selected from H, $C_1$-$C_6$ alkyl, $C_2$-$C_6$ alkenyl, $C_2$-$C_6$ alkynyl, F, —CN, —$N_3$; —$N(R^9)_2$, $C_1$-$C_6$ haloalkyl, $C_1$-$C_6$ hydroxyalkyl, $C_2$-$C_6$ alkenyl, $C_2$-$C_6$ alkynyl and $C_3$-$C_7$ cycloalkyl;

$R^8$ is selected from H and —$C(O)R^{13}$;

each occurrence of $R^9$ is independently selected from H, $C_1$-$C_6$ alkyl, $C_6$-$C_{10}$ aryl and $C_3$-$C_7$ cycloalkyl;

$R^{10}$, $R^{11}$ and $R^{12}$ are each independently selected from H, $C_1$-$C_6$ alkyl, $C_2$-$C_6$ alkenyl, $C_2$-$C_6$ alkynyl, $C_3$-$C_7$ cycloalkyl, halo, —$OR^{14}$, —$SR^{14}$, —$S(O)R^{14}$, —$S(O)_2R^{14}$, —$S(O)_2N(R^{14})_2$, —$NHC(O)OR^{14}$, —$NHC(O)N(R^{14})_2$, $C_1$-$C_6$ haloalkyl, $C_1$-$C_6$ hydroxyalkyl, —O—($C_1$-$C_6$ haloalkyl), —CN, —$NO_2$, —$N(R^{14})_2$, —NH($C_1$-$C_6$ alkylene)-(5- or 6-membered monocyclic heteroaryl), —NH($C_1$-$C_6$ alkylene)-(9- or 10-membered bicyclic heteroaryl), —$C(O)R^{14}$, —$C(O)OR^{14}$, —$C(O)N(R^{14})_2$ and —NHC(O)$R^{14}$;

each occurrence of $R^{13}$ is independently H or $C_1$-$C_6$ alkyl;

each occurrence of $R^{14}$ is independently selected from H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl); and each occurrence of m is independently 0 or 1.

Other embodiments, aspects and features of the present invention are either further described in or will be apparent from the ensuing description, examples, and appended claims.

DETAILED DESCRIPTION OF THE INVENTION

The present invention is directed to a process for making Nucleoside Phosphoramidate Compounds of Formula (I) which may be useful for inhibiting HCV NS5B polymerase, inhibiting the replication of HCV and for the treatment or prophylaxis of HCV infection.

Definitions and Abbreviations

The term "$C_1$-$C_6$ alkyl" as used herein, refers to an aliphatic hydrocarbon group, having from 1 to 6 carbon atoms wherein one of its hydrogen atoms is replaced with a bond. A $C_1$-$C_6$ alkyl group may be straight or branched. Non-limiting examples of $C_1$-$C_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. A $C_1$-$C_6$ alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, a $C_1$-$C_6$ alkyl group is linear. In another embodiment, a $C_1$-$C_6$ alkyl group is branched. Unless otherwise indicated, a $C_1$-$C_6$ alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms. The term "$C_1$-$C_3$ alkylene" refers to an alkylene group having from 1 to 3 carbon atoms.

The term "$C_6$-$C_{10}$ aryl" refers to phenyl and naphthyl. In one embodiment, an aryl group is phenyl.

The term "cycloalkyl" refers to a non-aromatic monocyclic or multicyclic ring system comprising from about 3 to about 14 ring carbon atoms. The term "3 to 7-membered cycloalkyl" refers to a monocyclic cycloalkyl group having from about 3 to about 7 ring carbon atoms. Examples of "3 to 7-membered cycloalkyl" groups include cyclopropyl, cyclobutyl, cyclopentyl, cyclohexyl and cycloheptyl. The term "7 to 14-membered cycloalkyl" refers to a multicyclic cycloalkyl group having from about 7 to about 14 ring carbon atoms. Examples of "7 to 14-membered cycloalkyl" groups include, but are not limited to adamantyl and octahydro indene. A cycloalkyl group can be optionally substituted with one or more "ring system substituents" which may be the same or different, and are as defined herein below. In one embodiment, a cycloalkyl group is unsubstituted. One or more ring carbon atoms of a cycloalkyl may be functionalized as a carbonyl group. An illustrative example of such a cycloalkyl (also referred to herein as a "cycloalkanoyl" group) includes, but is not limited to, cyclobutanoyl:

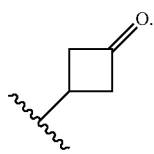 [SMILES: *C1CC(=O)C1]

The term "halo" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include imidazo[1,2-a]pyridinyl, imidazo[2,1-b]thiazolyl, benzofurazanyl, indolyl, azaindolyl, benzimidazolyl, benzothienyl, quinolinyl, benzimidazolyl, quinazolinyl, pyrrolopyridyl, imidazopyridyl, isoquinolinyl, benzoazaindolyl, benzothiazolyl, and the like, and all isomeric forms thereof. Unless otherwise indicated, a 9 or 10-membered bicyclic heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

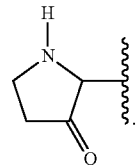 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic heterocycloalkyl" refers to a monocyclic heterocycloalkyl group having from 3 to 6 ring atoms. The term "4 to 7-membered monocyclic heterocycloalkyl" refers to a monocyclic heterocycloalkyl group having from 4 to 7 ring atoms. The term "7 to 11-membered bicyclic heterocycloalkyl" refers to a bicyclic heterocycloalkyl group having from 7 to 11 ring atoms. Unless otherwise indicated, a heterocycloalkyl group is unsubstituted.

The term "transition metal catalyst," as used herein, refers to a complex comprising a transition metal and one or more ligands, which are independently selected from any organic and/or any inorganic ligands.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between.

When any variable occurs more than one time in a compound involved in the process of the invention (e.g., $R^5$ or m), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds used as reactants or reagents in the processes of the invention (e.g., compounds of formulas (I) and (III)), a "stable" compound is one whose structure and properties remain or can be caused to remain essentially unchanged for a period of time sufficient to allow its use in the processes of the invention. In reference to Compound of Formula (II), a "stable" compound is a compound which can be prepared in accordance with the present invention and then isolated and whose structure and properties remain or can be caused to remain essentially unchanged for a period of time sufficient to allow use of the compound for its intended purpose; e.g., for use as a synthetic intermediate to make compounds capable of inhibiting HCV NS5B polymerase, and to make medicinally useful compounds, such as compounds useful for treating HCV infection in a subject.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

The Nucleoside Phosphoramidate Compounds can form salts which are also within the scope of this invention. The term "salt(s)", as used herein, denotes acidic salts formed with inorganic and/or organic acids, as well as basic salts formed with inorganic and/or organic bases. In addition, when a Nucleoside Phosphoramidate Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (II) may be formed, for example, by reacting a Nucleoside Phosphoramidate Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are considered equivalent to the free forms of the corresponding compounds for purposes of the invention. In one embodiment, the acid salts and base salts of the invention are intended to be pharmaceutically acceptable salts within the scope of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Nucleoside Phosphoramidate Compounds may be atropisomers (e.g., substituted biaryls) and are considered as part of this invention. Enantiomers can also be directly separated using chiral chromatographic techniques, such as chiral HPLC.

It is also possible that the Nucleoside Phosphoramidate Compounds may exist in different tautomeric forms, and all such stable forms are embraced within the scope of the invention. For example, all stable keto-enol and imine-enamine forms of the compounds are included in the invention.

All stereoisomers (for example, geometric isomers, optical isomers and the like) of the present compounds (including those of the salts, solvates, hydrates and esters of the compounds), such as those which may exist due to the presence of asymmetric carbon or phosphorus atoms, including enantiomeric forms (which may exist even in the absence of asymmetric carbons), rotameric forms, atropisomers, and diastereomeric forms, are contemplated within the scope of this invention. If a Nucleoside Phosphoramidate Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", and the like, is intended to apply equally to the salt, solvate and ester of enantiomers, diastereomers, rotamers, tautomers or racemates of the inventive compounds.

The following abbreviations are used below and have the following meanings: Ac is acetate, t-Bu is tertiary butyl, DCM is dichloromethane, DMSO is dimethylsulfoxide, Et₃N is triethylamine, EtOAc is ethyl acetate, HPLC is high performance liquid chromatography, iPrOAc and IPAc are isopropyl acetate, 2,6-lutidine is 2,6-dimethylpyridine, Me is methyl, MTBE is tert-butyl methyl ether, TFA is trifluoroacetic acid, THF is tetrahydrofuran and TLC is thin-layer chromatography.

The Process of the Present Invention

The present invention is directed to a process for making Nucleoside Phosphoramidate Compounds of Formula (II) which may be useful for inhibiting the replication of HCV and for the treatment or prophylaxis of HCV infection. One aspect of the present invention is the process for making Compounds of Formula (II) as set forth above in the Summary of the Invention ("Process A"):

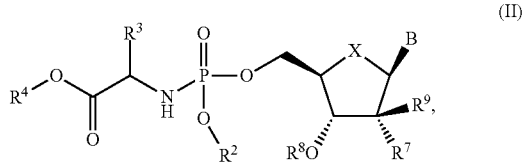
(II)

said process comprising the step of contacting a compound of formula (I):

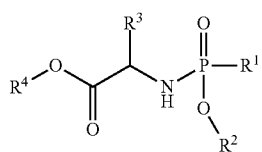
(I)

with a compound of formula (III):

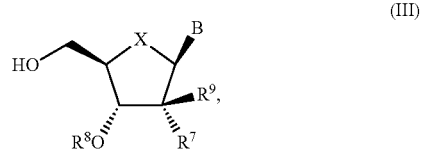
(III)

in the presence of an aluminum complex and a non-nucleophilic base, in an organic solvent A for a time and at a temperature sufficient to form the compound of formula (II), wherein:

X is O, S or $CH_2$;

B is a natural or non-natural purine or pyrimidine base, or B is selected from one of the following groups:

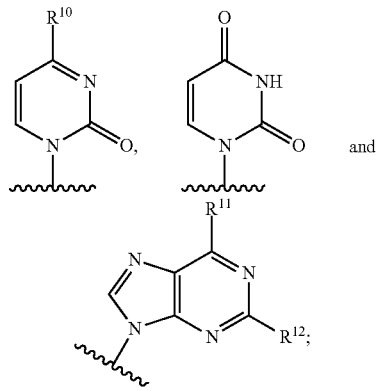

$R^1$ is selected from —O—($C_6$-$C_{10}$ aryl), 5 or 6-membered monocyclic heteroaryl, 9 or 10-membered bicyclic heteroaryl, —O-(5 or 6-membered monocyclic heteroaryl), —O-(9 or 10-membered bicyclic heteroaryl), —O-(4 to 7-membered monocyclic heterocycloalkyl), —S-(5 or 6-membered monocyclic heteroaryl), —S-(9 or 10-membered bicyclic heteroaryl), —S-(4 to 7-membered monocyclic heterocycloalkyl) or 10-membered heteroaryl) and —S—($C_6$-$C_{10}$ aryl), wherein any of said 5 or 6-membered monocyclic heteroaryl groups, any of said 9 or 10-membered bicyclic heteroaryl groups, any of said 4 to 7-membered monocyclic heterocycloalkyl groups, and any of said $C_6$-$C_{10}$ aryl groups can each be optionally substituted with one or more $R^5$ groups;

$R^2$ is selected from $C_6$-$C_{10}$ aryl, 5 or 6-membered monocyclic heteroaryl and 9 or 10-membered bicyclic heteroaryl, wherein said $C_6$-$C_{10}$ aryl group, said 5 or 6-membered monocyclic heteroaryl group and said 9 or 10-membered bicyclic heteroaryl group can be optionally substituted with one or more $R^5$ groups;

$R^3$ is selected from $C_1$-$C_6$ alkyl, $C_3$-$C_7$ cycloalkyl, phenyl or benzyl, wherein said $C_3$-$C_7$ cycloalkyl group, said phenyl group and the phenyl moiety of said benzyl group can be optionally substituted with one or more $R^5$ groups;

$R^4$ is selected from $C_1$-$C_6$ alkyl, $C_2$-$C_6$ alkenyl, —($C_1$-$C_3$ alkylene)$_m$-($C_3$-$C_{14}$ cycloalkyl) and —($C_1$-$C_3$ alkylene)$_m$-($C_6$-$C_{10}$ aryl);

each occurrence of $R^5$ is independently selected from —$C_1$-$C_6$ alkyl, halo, —$OR^6$, —$C(O)R^6$, —$CO_2R^6$, —$SR^6$, —$C_1$-$C_6$ haloalkyl, —$C_1$-$C_6$ hydroxyalkyl, —$N(R^6)_2$, —$S(O)R^6$, —$S(O)_2R^6$, —CN and —$NO_2$;

each occurrence of $R^6$ is independently H, $C_1$-$C_6$ alkyl, $C_1$-$C_6$ haloalkyl, $C_1$-$C_6$ hydroxyalkyl, —($C_1$-$C_3$ alkylene)$_m$-

($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) or —($C_1$-$C_3$ alkylene)$_m$-(9- or 10-membered bicyclic heteroaryl);

$R^7$ is selected from H, $C_1$-$C_6$ alkyl, $C_2$-$C_6$ alkenyl, $C_2$-$C_6$ alkynyl, F, —CN, —$N_3$, —N($R^9$)$_2$, $C_1$-$C_6$ haloalkyl, $C_1$-$C_6$ hydroxyalkyl, $C_2$-$C_6$ alkenyl, $C_2$-$C_6$ alkynyl and $C_3$-$C_7$ cycloalkyl;

$R^8$ is selected from H and —C(O)$R^{13}$;

each occurrence of $R^9$ is independently selected from H, $C_1$-$C_6$ alkyl, $C_6$-$C_{10}$ aryl and $C_3$-$C_7$ cycloalkyl;

$R^{10}$, $R^{11}$ and $R^{12}$ are each independently selected from H, $C_1$-$C_6$ alkyl, $C_2$-$C_6$ alkenyl, $C_2$-$C_6$ alkynyl, $C_3$-$C_7$ cycloalkyl, halo, —O$R^{14}$, —S$R^{14}$, —S(O)$R^{14}$, —S(O)$_2$$R^{14}$, —S(O)$_2$N($R^{14}$)$_2$, —NHC(O)O$R^{14}$, —NHC(O)N($R^{14}$)$_2$, $C_1$-$C_6$ haloalkyl, $C_1$-$C_6$ hydroxyalkyl, —O—($C_1$-$C_6$ haloalkyl), —CN, —$NO_2$, —N($R^{14}$)$_2$, —NH($C_1$-$C_6$ alkylene)-(5- or 6-membered monocyclic heteroaryl), —NH($C_1$-$C_6$ alkylene)-(9- or 10-membered bicyclic heteroaryl), —C(O)$R^{14}$, —C(O)O$R^{14}$, —C(O)N($R^{14}$)$_2$ and —NHC(O)$R^{14}$;

each occurrence of $R^{13}$ is independently H or $C_1$-$C_6$ alkyl;

each occurrence of $R^{14}$ is independently selected from H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl); and each occurrence of m is independently 0 or 1.

In one embodiment, X is O.

In one embodiment, B is a natural or non-natural pyrimidine base.

In another embodiment, B is:

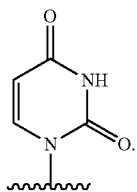 [SMILES: *n1ccc(=O)[nH]c1=O]

In one embodiment, $R^1$ is selected from —O—($C_6$-$C_{10}$ aryl), —O-(5 or 6-membered monocyclic heteroaryl) and —S—($C_6$-$C_{10}$ aryl), wherein said 5 or 6-membered monocyclic heteroaryl group or any of said $C_6$-$C_{10}$ aryl groups can be optionally substituted with up to 5 groups, each independently selected from $C_1$-$C_6$ alkyl, —$NO_2$, halo and $C_1$-$C_6$ haloalkyl.

In one embodiment, $R^1$ is —O—($C_6$-$C_{10}$ aryl), which can be optionally substituted with up to 5 groups, each independently selected from —$NO_2$ and halo.

In another embodiment, $R^1$ is —O-(5 or 6-membered monocyclic heteroaryl), which can be optionally substituted with up to 5 groups, each independently selected from halo.

In another embodiment, $R^1$ is —S—($C_6$-$C_{10}$ aryl), which can be optionally substituted with up to 5 groups, each independently selected from halo.

In another embodiment, $R^1$ is —O-phenyl or —O-pyridyl, each of which can be optionally substituted with up to 5 groups, each independently selected from F, Cl and —$NO_2$.

In one embodiment, $R^1$ is pentafluorophenoxy.

In another embodiment, $R^1$ is:

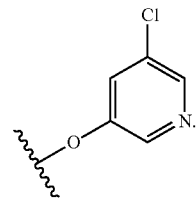

In one embodiment, $R^2$ is $C_6$-$C_{10}$ aryl, which can be optionally substituted as set forth in formula (I) of Process A.

In another embodiment, $R^2$ is unsubstituted phenyl.
In one embodiment, $R^3$ is $C_1$-$C_6$ alkyl.
In one embodiment, $R^4$ is $C_1$-$C_6$ alkyl.
In one embodiment, $R^3$ and $R^4$ are each independently $C_1$-$C_6$ alkyl.
In another embodiment, $R^3$ is methyl.
In another embodiment, $R^4$ is isopropyl.
In still another embodiment, $R^3$ is methyl and $R^4$ is isopropyl.
In yet another embodiment, $R^2$ is unsubstituted phenyl, $R^3$ is methyl and $R^4$ is isopropyl.

In one embodiment, X is O and $R^1$ is a —O—($C_6$-$C_{10}$ aryl) group, optionally substituted with up to 5 groups, each independently selected from $NO_2$ and F.

In another embodiment, X is O and $R^1$ is pentafluorophenoxy.

In another embodiment, X is O; $R^1$ is a —O—($C_6$-$C_{10}$ aryl) group, optionally substituted with up to 5 groups, each independently selected from $NO_2$ and F; $R^2$ is unsubstituted phenyl; and $R^3$ and $R^4$ are each independently $C_1$-$C_6$ alkyl.

In another embodiment, X is O; $R^1$ is a —O—($C_6$-$C_{10}$ aryl) group, optionally substituted with up to 5 groups, each independently selected from $NO_2$ and F; $R^2$ is unsubstituted phenyl; $R^3$ is methyl; and $R^4$ is isopropyl In one embodiment, X is O; B is a pyrimidine base; $R^9$ is methyl; $R^7$ is selected from F, —CN, $C_2$-$C_6$ alkynyl, —$NH_2$ and —$N_3$; and $R^8$ is H or —C(O)CH(CH$_3$)$_2$.

In another embodiment, $R^9$ is methyl; B is uridine; $R^7$ is selected from F, $C_2$-$C_6$ alkynyl, and —CN; and $R^8$ is H or —C(O)CH(CH$_3$)$_2$.

In another embodiment, $R^9$ is methyl; B is uridine; $R^7$ is —CN and $R^8$ is —C(O)CH(CH$_3$)$_2$.

In still another embodiment, $R^9$ is methyl; B is uridine; $R^7$ is —C≡CH; and $R^8$ is —H.

In another embodiment, $R^9$ is methyl; B is uridine; $R^7$ is —F and $R^8$ is —H.

In one embodiment, the compound of formula (I) used in Process A has the formula (Ia) or (Ib):

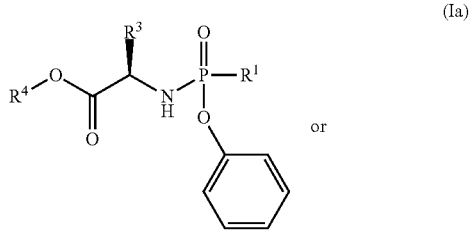

(Ia)

or

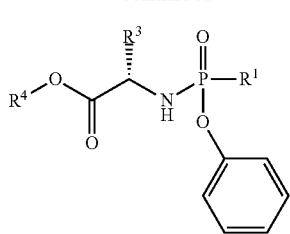
(Ib)

wherein:

R[1] is selected from —O—($C_6$-$C_{10}$ aryl), —O-(5 or 6-membered monocyclic heteroaryl) and —S—($C_6$-$C_{10}$ aryl), wherein said 5 or 6-membered monocyclic heteroaryl group or any of said $C_6$-$C_{10}$ aryl groups can be optionally substituted with up to 5 groups, each independently selected from $C_1$-$C_6$ alkyl, —$NO_2$, halo, $C_1$-$C_6$ haloalkyl;

R[3] is —$C_1$-$C_6$ alkyl; and

R[4] is —$C_1$-$C_6$ alkyl.

In another embodiment, the compound of formula (I) used in Process A has the formula (Ia'), (Ia"), (Ib') or (Ib"):

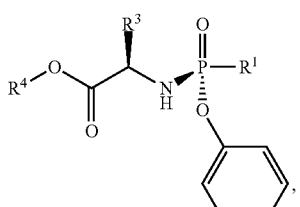
(Ia')

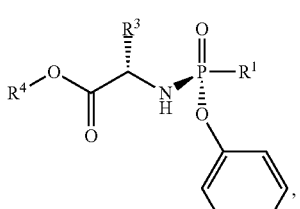
(Ib')

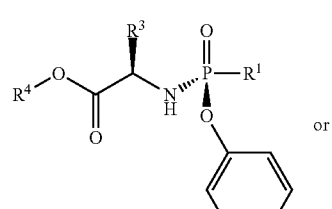
(Ia")
or

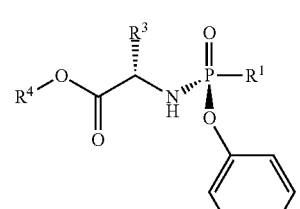
(Ib")

wherein:

R[1] is selected from —O—($C_6$-$C_{10}$ aryl), —O-(5 or 6-membered monocyclic heteroaryl) and —S—($C_6$-$C_{10}$ aryl), wherein said 5 or 6-membered monocyclic heteroaryl group or any of said $C_6$-$C_{10}$ aryl groups can be optionally substituted with up to 5 groups, each independently selected from $C_1$-$C_6$ alkyl, —$NO_2$, halo and $C_1$-$C_6$ haloalkyl;

R[3] is —$C_1$-$C_6$ alkyl; and

R[4] is —$C_1$-$C_6$ alkyl.

In another embodiment, the compound of formula (I) used in Process A has the structure:

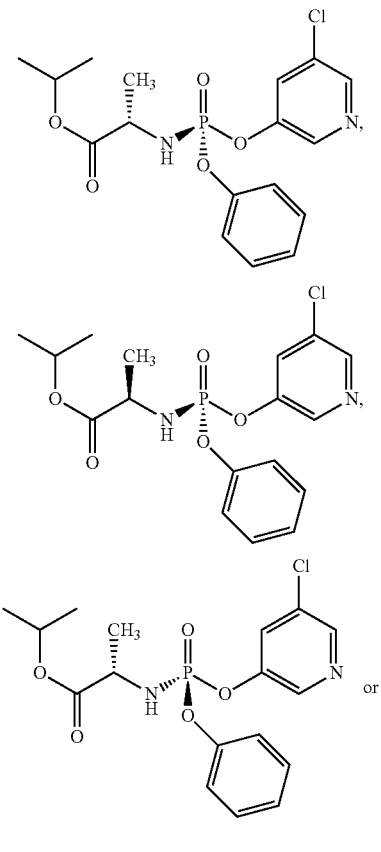

In another embodiment, the compound of formula (I) used in Process A has the structure:

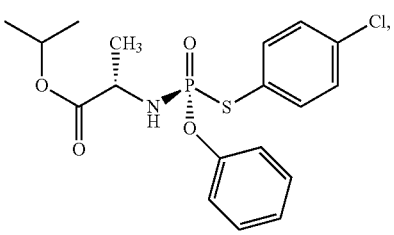

-continued

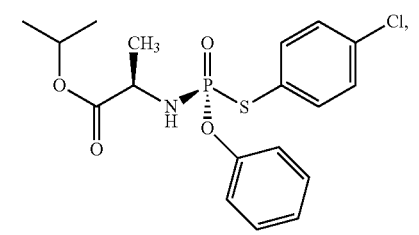

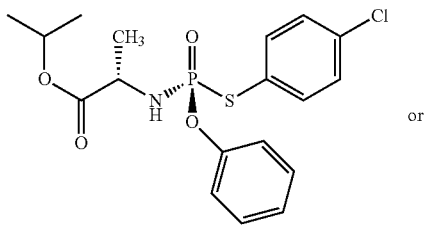
or

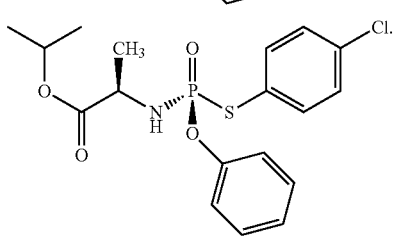

In another embodiment, the compound of formula (I) used in Process A has the structure:

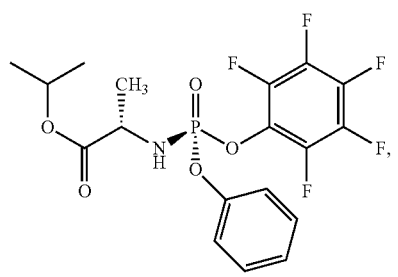

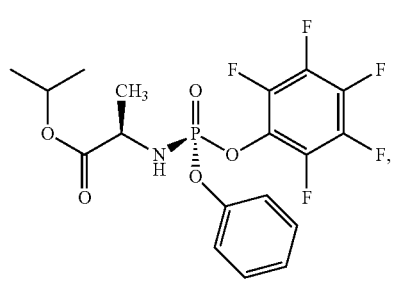 [SMILES: CC(C)OC(=O)[C@@H](C)N[P@](=O)(Oc1ccccc1)Oc1c(F)c(F)c(F)c(F)c1F]

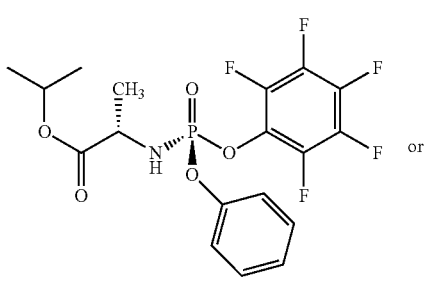
or

-continued

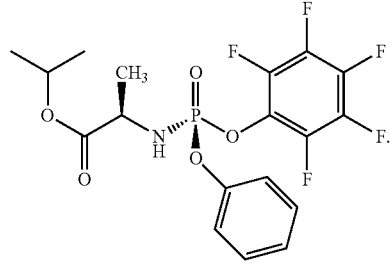

In another embodiment, the compound of formula (I) used in Process A has the structure:

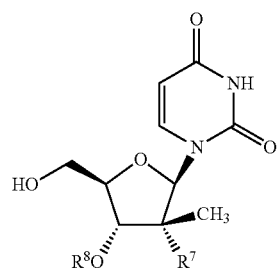

In one embodiment, the compound of formula (III) used in Process A is a compound of formula (IIIa):

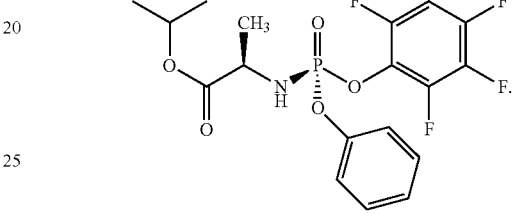

(IIIa)

wherein $R^7$ is selected from F, —CN, $C_2$-$C_6$ alkynyl, —$NH_2$ and —$N_3$; and $R^8$ is H or —C(O)CH($CH_3$)$_2$.

In one embodiment, for the compound of formula (III) or (IIIa), $R^7$ is selected from F, —C≡CH, —$N_3$ and —$NH_2$, and $R^8$ is H.

In another embodiment, for the compound of formula (III) or (IIIa), $R^7$ —CN and $R^8$ is —C(O)CH($CH_3$)$_2$.

In one embodiment, organic solvent A is selected from toluene, THF, DCM, MTBE, DMF, propylene carbonate, DME, 1,3-dimethyl-3,4,5,6-tetrahydro-2(1H)-pyrimidinone, 2-methyltetrahydrofuran, xylenes, ethyl acetate, NMP, anisole, isopropyl acetate, acetonitrile and mixtures thereof.

In another embodiment, organic solvent A is selected from toluene, dichloromethane, benzene, tetrahydrofuran, 2-methyl tetrahydrofuran, ethyl acetate and acetonitrile.

In another embodiment, organic solvent A is tetrahydrofuran.

In yet another embodiment, Process A can be conducted in any organic solvent.

In one embodiment, the non-nucleophilic base used in Process A is a DBU, DBN, pyridine, 2,6-lutidine, tetramethyl guanidine or a phosphazene derived base.

In another embodiment, the non-nucleophilic base used in Process A is an organic amine.

In another embodiment, the base used in Process A is 2,6-lutidine.

In still another embodiment, the base used in Process A is 2,6-lutidine and organic solvent A is THF.

In one embodiment, the aluminum complex used in Process A has the formula Al(—O—$C_1$-$C_6$ alkyl)$_3$, ($C_1$-$C_6$ alkyl)$_3$Al, ($C_1$-$C_6$ alkyl)$_2$AlCl or ($C_1$-$C_6$ alkyl)AlCl$_2$.

In another embodiment, the aluminum complex used in Process A is has the formula ($C_1$-$C_6$ alkyl)$_2$AlCl or Al(—O—($C_1$-$C_6$ alkyl))$_3$.

In one embodiment, the aluminum complex used in Process A is $(CH_3)_2AlCl$ or Al(t-BuO)$_3$.

In another embodiment, the aluminum complex used in Process A is $AlCl_3$.

In another embodiment, the aluminum complex used in Process A is $(CH_3)_2AlCl$.

In still another embodiment, the aluminum complex used in Process A is Al(Ot-Bu)$_3$.

In one embodiment, the aluminum complex used in Process A is $AlCl_3$ and the base used in Process A is 2,6-lutidine.

In another embodiment, the aluminum complex used in Process A is $(CH_3)_2AlCl$ and the base used in Process A is 2,6-lutidine.

In another embodiment, the aluminum complex used in Process A is Al(Ot-Bu)$_3$ and the base used in Process A is 2,6-lutidine.

In one embodiment, Process A is conducted at a temperature in a range of from about −40° C. to about 120° C.

In another embodiment, Process A is conducted at a temperature in a range of from about 0° C. to about 100° C.

In another embodiment, Process A is conducted at a temperature in a range of from about 20° C. to about 80° C.

In still another embodiment, Process A is conducted at a temperature in a range of from about 25° C. to about 65° C.

In one embodiment, for Process A:
the organic solvent A is THF;
the base used is an organic amine;
the aluminum complex used is a compound of formula Al(—O—$C_1$-$C_6$ alkyl)$_3$ or ($C_1$-$C_6$ alkyl)$_2$AlCl; and
the process is conducted at a temperature in a range of from about 0° C. to about 100° C.

In another embodiment, for Process A:
the organic solvent A is THF;
the base used is 2,6-lutidine;
the aluminum complex used is $(CH_3)_2AlCl$ or Al(Ot-Bu)$_3$;
the process is conducted at a temperature in a range of from about 20° C. to about 80° C.; and
the compound of formula (I) used has the formula (Ia) or (Ib):

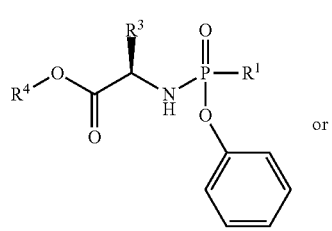

(Ia)

or

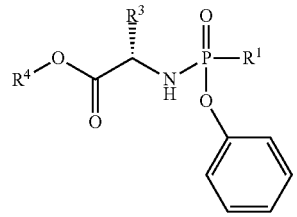

(Ib)

wherein:
$R^1$ is —O-phenyl, —O-pyridyl or —S-phenyl wherein said phenyl or pyridyl groups can each be optionally substituted with up to 5 groups, each independently selected from $C_1$-$C_6$ alkyl, —$NO_2$, halo and $C_1$-$C_6$ haloalkyl;
$R^3$ is —$C_1$-$C_6$ alkyl; and
$R^4$ is —$C_1$-$C_6$ alkyl.

In another embodiment, for Process A:
the organic solvent A is THF;
the base used is 2,6-lutidine;
the aluminum complex used is $(CH_3)_2AlCl$ or Al(Ot-Bu)$_3$;
the process is conducted at a temperature in a range of from about 20° C. to about 60° C.; and
the compound of formula (I) used has the formula (Ia'), (Ia"), (Ib') or (Ib"):

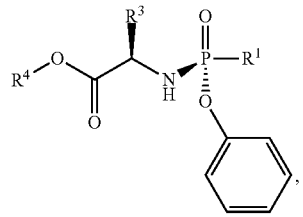

(Ia')

,

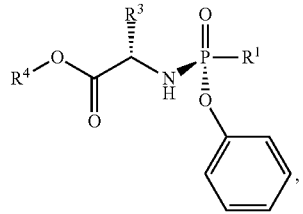

(Ib')

,

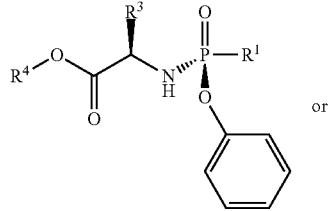

(Ia")

or

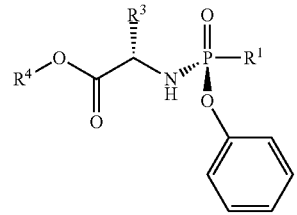

(Ib")

wherein:
R[1] is pentafluorophenoxy;
R[3] is —$C_1$-$C_6$ alkyl; and
R[4] is —$C_1$-$C_6$ alkyl.
In one embodiment, the compound of formula (II) that is made by said process is selected from:
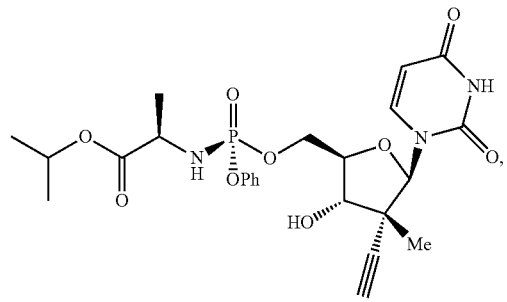
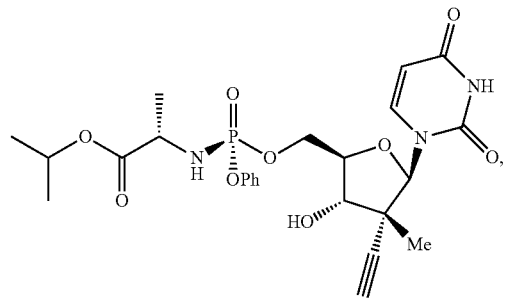
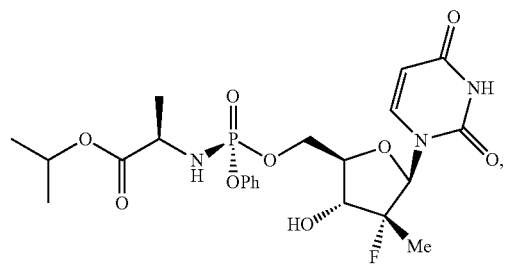
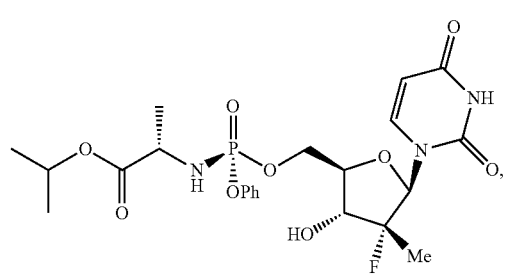
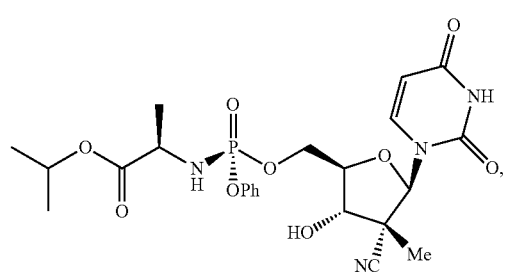
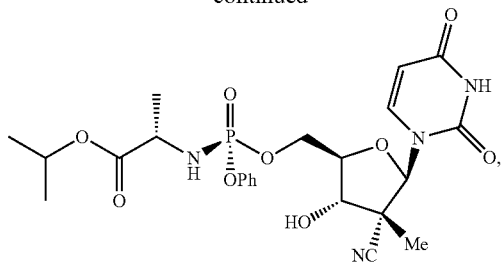
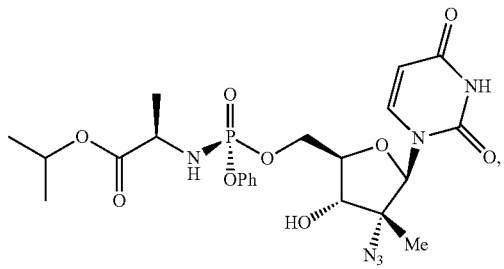
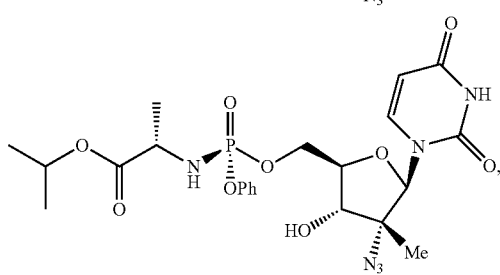
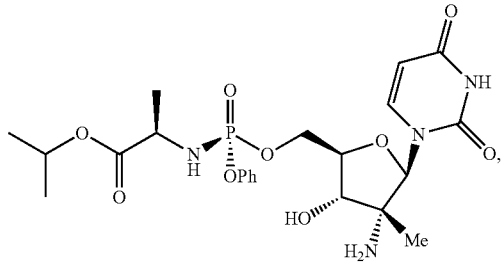
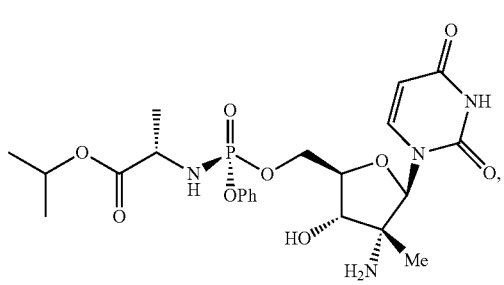
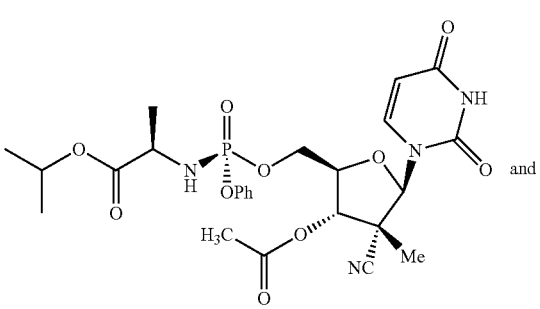

-continued

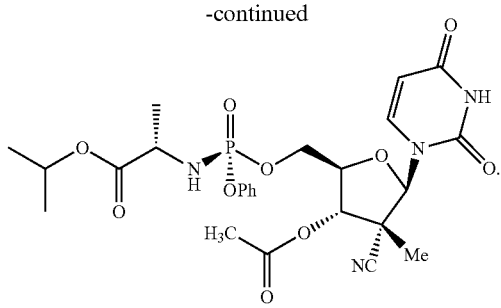

EXAMPLES

General Methods

Solvents, reagents, and intermediates that are commercially available were used as received. Reagents and intermediates that are not commercially available were prepared in the manner as described below. $^1$H NMR spectra were obtained on a Bruker Ultrashield 400 (400 MHz) and are reported as ppm downfield from Me$_4$Si with number of protons, multiplicities, and coupling constants in Hertz indicated parenthetically. Where LC/MS data are presented, analyses was performed using an Agilent 1100 LCMS system with LC column: Ascentis Express C18, 2.7 micron, 150 mm×3 mm ID; gradient flow: 0 minutes—10% CH$_3$CN/2 mM aqueous NH$_4$COOH/HCOOH, 6 minutes—95% CH$_3$CN, 6-12 minutes—95% CH$_3$CN, 14 minutes—stop. The observed parent ion is given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

General Preparation of Compounds of Formula (I)

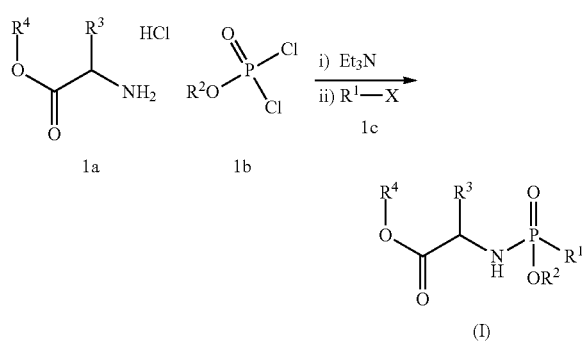

A compound of formula 1a (19.22 g, 115 mmol) is charged to an inerted overhead stirred jacketed vessel followed by a suitable organic solvent (100-200 mL) to provide a solution which is then cooled to about −20° C. A solution of a compound of formula 1b (25.0 g, 1.0 eq.) in a suitable organic solvent (100-200 mL) is then added while maintaining internal temperature below −10° C. and the resulting solution is then cooled back to −20° C. To the cooled solution is added a suitable base (3.2 eq.) over 60 minutes with further cooling to control the resulting exotherm and maintain the internal reaction temperature below −17° C. The resulting reaction was re-cooled to −20° C. and allowed to stand at this temperature without stirring for 30 minutes. A solution of compound 1c (1.0 eq.) in a suitable organic solvent (100-200 mL) is then added to the reaction over a period of 75 minutes and the resulting reaction is allowed to age at −20° C. until the reaction has progressed to a suitable point. The reaction mixture is then warmed to room temperature and the resulting slurry is filtered. The collected solid is then washed with THF (2×100 mL) and the filtrates are combined to provide a solution of a compound of formula (I) (typically 80-90% yield). The Compounds of Formula (I) so obtained can then be further purified using workup, crystallization or chromatography methods well-known to those skilled in the art of organic synthesis.

General Workup Procedure for Compounds of Formula (I)

A solution of a compound of formula (I), obtained using the method described above, is diluted with MTBE (or other organic non water miscible solvents such as EtOAc and IPAc), then washed sequentially with an aqueous hydrochloric acid (2×), aqueous sodium hydrogencarbonate (2×), then water. The organic phase can then be concentrated in vacuo to provide a compound of formula (I).

General Crystallization Method for Purifying Compounds of Formula (I)

On concentration several products 1d form solids. These can be crystallized by those skilled in the art typically involving a solubilizing organic solvent such as MTBE, EtOAc, IPAc and an anti-solvent typically hexane or heptane. Often one isomer of the products 1d is less soluble than others and the solid product which can be isolated using filtration is enhanced in this less soluble isomer giving a purity upgrade.

Purification of Compounds of Formula (I) Using Chromatography

Pure single stereoisomers of the compounds of formula (I) can be isolated using chromatographic techniques well-known to those skilled in the art of organic synthesis, such as thin-layer chromatography, flash column chromatography on silica gel, MPLC or HPLC.

Example 2

Preparation of Compound 1

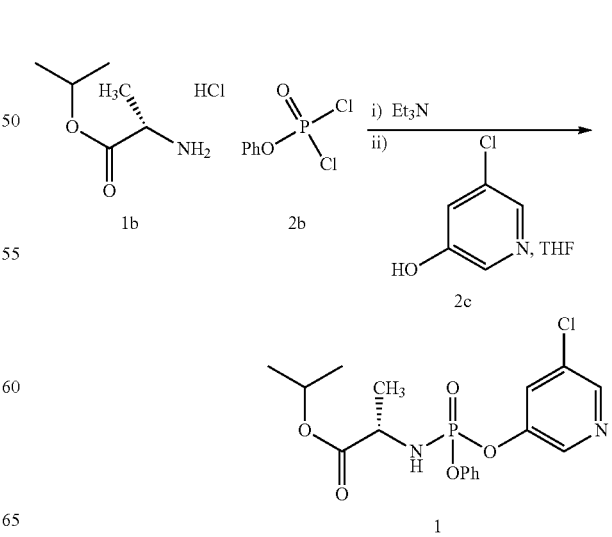

Compound 2a hydrochloride salt (19.22 g, 115 mmol) was charged to an inerted overhead stirred jacketed vessel. To the vessel was then added THF (125 mL) and the resulting solution was cooled to −20° C. A solution of compound 2b (25.0 g, 114 mmol) in THF (125 mL) was then added to the compound 2a solution, while maintaining the internal reaction temperature below −10° C. during the course of the addition. The resulting solution was then cooled to −20° C. and triethylamine (51.2 mL, 367 mmol) was added over a 60 minute period with further cooling used to control the resulting exotherm and maintain the internal reaction temperature below −17° C. during the course of the addition. The resulting reaction was then cooled to −20° C. and allowed to age for 30 minutes at this temperature. A solution of compound 2c
(114 mmol) in THF (150 mL) was then added to the reaction over a 75 minute period and resulting reaction was allowed to age at −20° C. until monitoring via HPLC indicated >98% consumption of the starting materials. The reaction mixture was then warmed to room temperature and the resulting slurry was filtered to remove triethylamine hydrochloride. The resulting filter cake was washed with THF (2×100 mL) and the filtrates were combined to provide a solution of compound 1 as a mixture of diastereomers (80% yield).

Example 3

Procedure for Purifying Compound 1 Via Crystallization

Compound 1A
$^1$H NMR (400 MHz, CDCl3): δ 8.45-8.40 (m, 2H), 7.71-7.68 (m, 1H), 7.40-7.32 (m, 2H), 7.27-7.18 (m, 3H), 5.0286 (heptet, J=6.3 Hz, 1H), 4.17-4.06 (m, 1H), 4.01-3.86 (m, 1H), 1.42 (d, J=7.0 Hz, 3H), 1.25 (d, J=5.86 Hz, 3H), 1.24 (d, 5.87 Hz, 3H).
$^{13}$C NMR (100 MHz, CDCl$_3$): δ 172.45 (d, J=9.1 Hz), 150.20 (d, J=6.8 Hz), 147.56 (d, J=6.8 Hz), 145.19, 140.23 (d, J=6.1 Hz), 131.96, 129.90, 127.84 (d, J=4.6 Hz), 125.55, 120.11 (d, J=4.6 Hz), 69.65, 50.60 (d, J=1.6 Hz), 21.64 (d, J=6.9 Hz), 21.03 (d, J=3.8 Hz).
$^{31}$P NMR (162 MHz, CDCl$_3$): δ −2.261 (+trace at −24.128)
Compound 1B
$^1$H NMR (400 MHz, CDCl3): δ 7.36-7.30 (m, 2H), 7.26-7.21 (m, 2H), 7.18-7.13 (m, 1H), 5.04 (heptet, J=6.26 Hz, 1H), 4.81-4.69 (m, 1H), 4.01-3.90 (m, 1H), 3.53 (t, J=10.17 Hz, 1H), 1.37 (d, J=7.04 Hz, 3H), 1.35 (d, J=6.26 Hz, 3H), 1.33 (d, J=6.26 Hz, 3H), 1.26 (d, J=6.26 Hz, 3H), 1.25 (d, J=6.26 Hz, 3H).
$^{13}$C NMR (100 MHz, CDCl$_3$): δ 173.052 (d, J=7.6 Hz), 151.000 (d, J=6.9 Hz), 129.574, 124.636, 120.217 (d, J=5.3 Hz), 72.380 (d, J=5.3 Hz), 69.119, 50.359, 23.728 (d, J=7.6), 23.683 (d, J=7.6 Hz), 21.717, 21.640, 21.107 (d, J=4.6 Hz).
$^{31}$P NMR (162 MHz, CDCl$_3$): δ 1.3449.

Example 4

Procedure for Purifying Compound 2 Via Crystallization

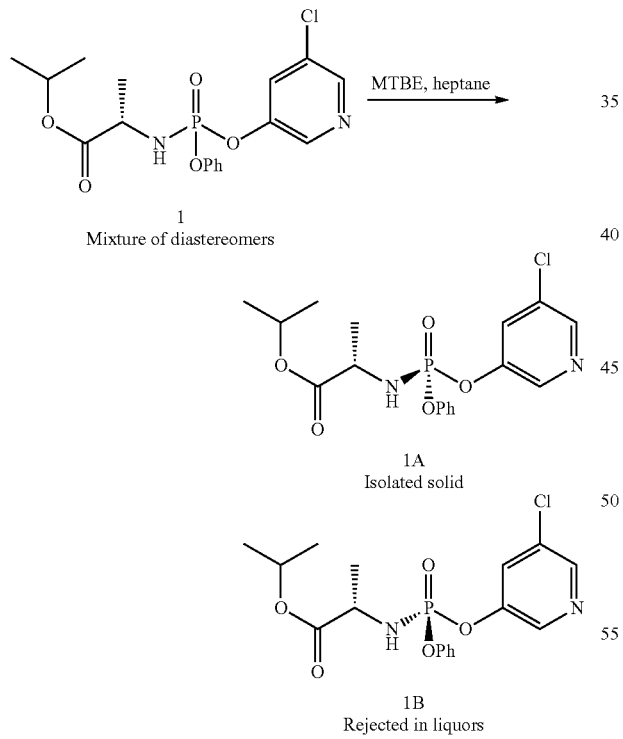

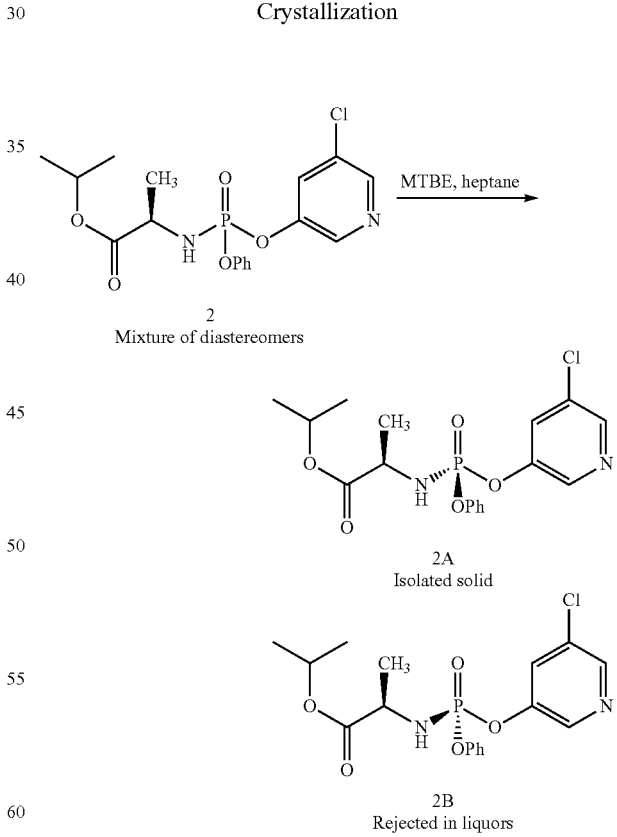

A solution of compound 1 (obtained using the method described in Example 2) was concentrated in vacuo. The resulting residue was triturated with a mixture of MTBE in heptane (10 mL/g) and agitated until a thick slurry was formed. Filtration of the slurry provided compound 1A as a white solid >98:2 dr (30-35%). Compound 1B was isolated directly from the liquors.

A solution of compound 2 (obtained using the method described in Example 2 and substituting the enantiomer of compound 2a in place of compound 2a) was concentrated in vacuo. The resulting residue was triturated with a mixture of MTBE in heptane (10 mL/g) and agitated until a thick slurry was formed. Filtration of the slurry provided compound 2A as a white solid >99:1 dr (30-35%). Compound 2B was isolated directly from the liquors.

Compound 2A $^1$H NMR (500 MHz, CDCl3): δ 8.45-8.40 (m, 2H), 7.71-7.68 (m, 1H), 7.40-7.32 (m, 2H), 7.27-7.18 (m, 3H), 5.02 (heptet, J=5.7 Hz, 1H), 4.17-4.06 (m, 1H), 4.01-3.86 (m, 1H), 1.41 (d, J=6.7 Hz, 3H), 1.24 (d, J=5.4 Hz, 3H), 1.23 (d, 5.4 Hz, 3H).

$^{13}$C NMR (125 MHz, CDCl$_3$): δ 172.45 (d, J=8.0 Hz), 150.20 (d, J=6.3 Hz), 147.56 (d, J=6.3 Hz), 145.18, 140.23 (d, J=5.8 Hz), 131.95, 129.90, 127.84 (d, J=4.3 Hz), 125.54, 120.11 (d, J=4.3 Hz), 69.65, 50.60 (d, J=1.3 Hz), 21.63 (d, J=6.3 Hz), 21.02 (d, J=3.2 Hz).

$^{31}$P NMR (202 MHz, CDCl$_3$): δ −2.41

Compound 2B $^1$H NMR (400 MHz, CDCl3): δ 7.36-7.30 (m, 2H), 7.26-7.21 (m, 2H), 7.18-7.13 (m, 1H), 5.037 (heptet, J=6.26 Hz, 1H), 4.81-4.69 (m, 1H), 4.01-3.90 (m, 1H), 3.5309 (t, J=10.17 Hz, 1H), 1.3742 (d, J=7.04 Hz, 3H), 1.35175 (d, J=6.26 Hz, 3H), 1.33025 (d, J=6.26 Hz, 3H), 1.25885 (d, J=6.26 Hz, 3H), 1.253 (d, J=6.26 Hz, 3H).

$^{13}$C NMR (100 MHz, CDCl$_3$): δ 173.0.52 (d, J=7.6 Hz), 151.000 (d, J=6.9 Hz), 129.574, 124.636, 120.217 (d, J=5.3 Hz), 72.380 (d, J=5.3 Hz), 69.119, 50.359, 23.728 (d, J=7.6), 23.683 (d, J=7.6 Hz), 21.717, 21.640, 21.107 (d, J=4.6 Hz).

$^{31}$P NMR (162 MHz, CDCl$_3$): δ 1.3449.

Example 5

Alternate Procedure for Purifying Compound 1 Via Crystallization

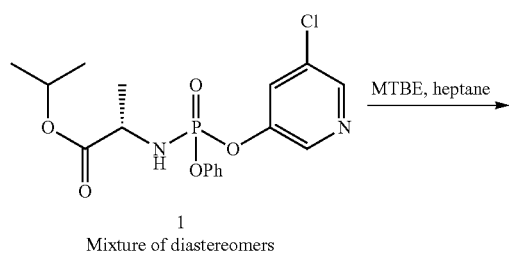

A solution of compound 1 was concentrated in vacuo. The resulting residue was dissolved in MTBE (2 mL/g) and heated to 40° C. n-heptane (10 mL/g) was then added over 3 hours with seeding after ~2 mL/g heptane was added. A thick slurry resulted, which was then cooled to room temperature. Subsequent filtration of the slurry provided compound 1A as a white solid in greater than >98:2 dr (~35% isolated yield).

Example 6

Procedure for Making Compounds 3A and 3B

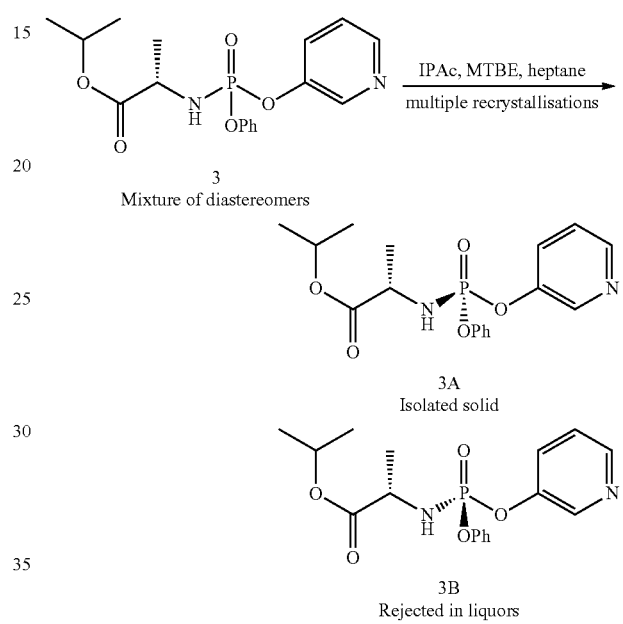

Trituration of compound 3 (made using the method described in Example 2 and substituting 4-hydroxy pyridine for compound 2c) with a mixture of IPAc, MTBE and heptane provided a slurry with the solid enhanced in diastereomer 3A. Following isolation and recrystallisations from IPAc-heptane, compound 3A was isolated in 96.2:3.8 dr Example 7

Alternate Procedure for Purifying Compound 1 Via Crystallization

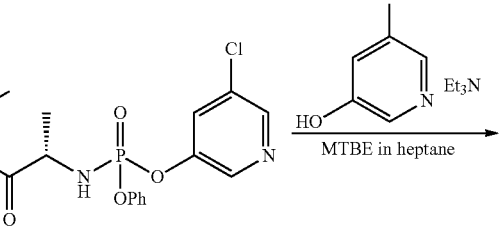

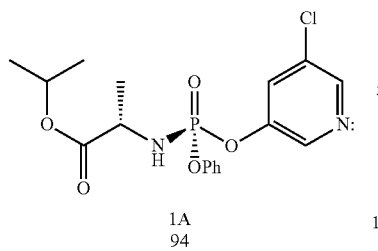

1A
94

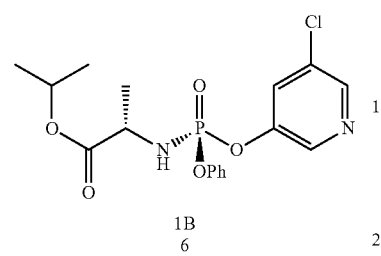

1B
6

Compound 1 was added to a mixture of 5% MTBE in heptane (10 mL/g), forming a slurry. Addition of 0.1 equiv 5-chloro-3-hydroxypyridine and 1 equiv triethylamine to the slurry allowing the resulting mixture to age at room temperature for 4 days provided a 94:6 mixture of 1A:1B. Addition of aqueous HCl and IPAc forms a biphasic mixture. The organic layer was washed with aqueous HCl, aqueous sodium hydrogen carbonate and then water. Solvent switching the organic layer into a 5% IPAc in heptane mixture (10 volumes) and filtration provided 1A in >99.5:0.5 dr.

Example 8

Preparation of Compound A

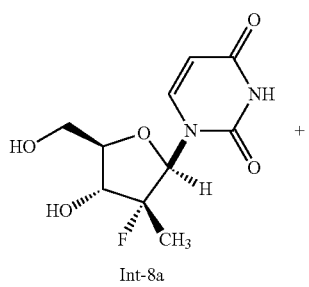

Int-8a

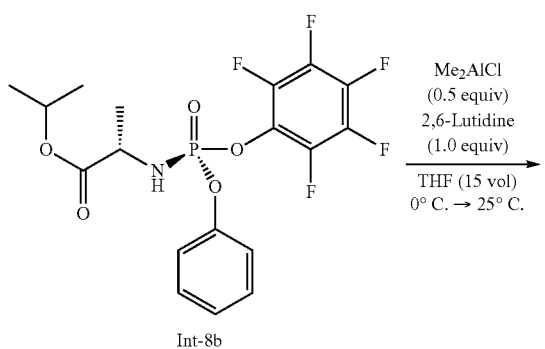

Int-8b

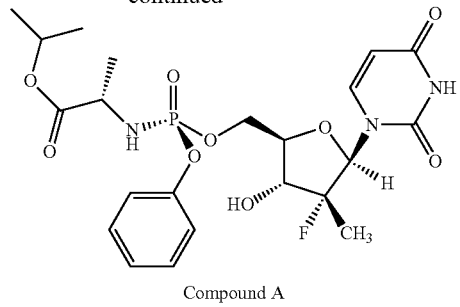

Compound A

A solution of Int-8a (4.68 g, 18.0 mmol, made using the methods described in U.S. Pat. No. 8,906,880) and Int-8b (9.79 g, 21.60 mmol, made using the methods described in International Publication No. WO 2014/062596) in THF (70.3 mL) was cooled to 0° C. and to the cooled solution was added dimethylaluminum chloride as a 1M solution in hexanes (10.00 mL, 9.00 mmol, 9 mL) followed by 2,6-lutidine (2.096 mL, 18.00 mmol). The reaction mixture was allowed to warm to room temperature then stir at that temperature for 16 hours, at which time the reaction appears to have reached 85% conversion with a 38:1 dr and 41:1 mono:bis ratio. The reaction mixture was then heated to 45° C. and allowed to stir at this temperature for 4 hours. The reaction mixture was then diluted with isopropyl acetate (10 vol) and quenched with 30% aqueous tartaric acid (10 vol). The reaction mixture was transferred to a separatory funnel and the organic phase was collected and washed sequentially with 30% aqueous tartaric acid (5 vol) and brine (5 vol), the dried over magnesium sulfate, filtered, and concentrated in vacuo. The resulting residue was purified using isco chromatography (0-8% methanol in dichloromethane) and the collected product was dried in vacuo. The product was then triturated with dichloromethane/hexanes and concentrated in vacuo and the product was dried overnight under vacuum to provide Compound A as a white, amorphous solid (8.18 g, 86% yield). HPLC indicates a 25:1 diastereomeric ratio. $^1$H NMR (500 MHz, DMSO-$d_6$): δ 11.53 (s, 1H), 7.57-7.56 (m, 1H), 7.39-7.36 (m, 2H), 7.23-7.17 (m, 3H), 6.08-6.03 (m, 2H), 5.86 (m, 1H), 5.54 (d, J=10 Hz, 1H), 4.88-4.83 (m, 1H), 4.38-4.35 (m, 1H), 4.25-4.23 (m, 1H), 4.02-3.99 (m, 1H), 3.85-3.78 (m, 2H), 1.27-1.22 (m, 6H), 1.16 (d, J=5.0 Hz, 6H).

Example 9

Preparation of Compound B

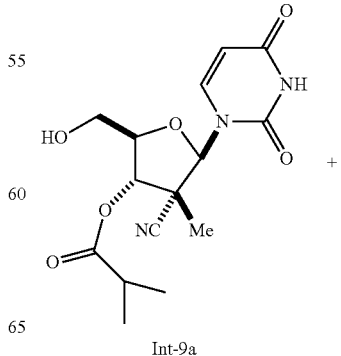

Int-9a

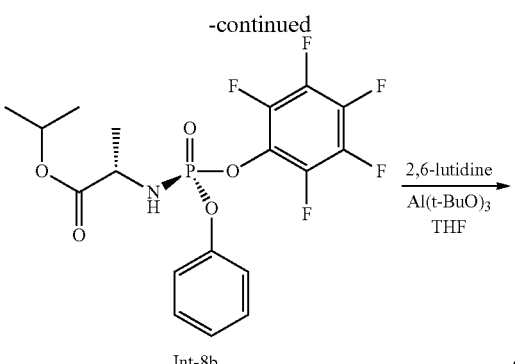

Int-8b

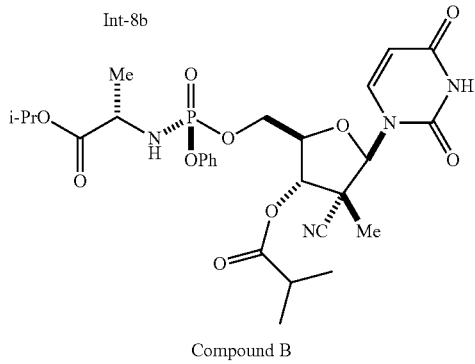

Compound B

To a solution of compound Int-9a (0.63 g, 1.494 mmol, 80 wt %, made using the methods described in International Publication No. WO 2014/062596) in tetrahydrofuran (7.56 mL), was added compound Int-8b (0.813 g, 1.793 mmol, made using the methods described in International Publication No. WO 2014/062596). To the resulting solution was added 2,6-dimethylpyridine (0.261 mL, 2.241 mmol) followed by a solution of tri-tert-butoxyaluminum (0.184 g, 0.747 mmol) in THF (1 mL). The resulting reaction was allowed to age for about 15 hours at room temperature then was quenched with aqueous L-tartaric acid solution. The resulting mixture was transferred to a separatory funnel and the organic layer was collected and diluted with isopropyl acetate. The aqueous layer was extracted with isopropyl acetate (2×5 mL). The combined organic layers were then washed with 5% brine (2×10 mL), then dried over magnesium sulfate, filtered and concentrated in vacuo. The resulting residue was crystallized from isopropyl acetate/n-heptane to provide compound B (0.78 g, 86%). $^1$H NMR (CDCl$_3$) δ 9.22 (s, 1H), 7.58 (d, J=7.2 Hz, 1H), 7.35 (d, J=8.2 Hz, 1H), 7.33 (d, J=8.2 Hz, 1H), 7.24-7.22 (m, 2H), 7.23-7.19 9 (m, 1H), 6.35 (s, 1H), 5.61 (d, J=8.2 Hz, 1H), 5.07 (d, J=6.4 Hz, 1H), 5.03 (ddd, J=12.2, 6.1, 6.1 Hz, 1H), 4.51 (ddd, J=12.1, 7.1, 2.0 Hz, 1H), 4.24 (ddd, J=10.4, 7.5, 2.8 Hz, 1H), 4.21-4.17 (m, 1H), 4.04-3.92 (m, 2H), 2.75-2.66 (m, 1H), 1.39 (d, J=6.8 Hz, 3H), 1.28-1.23 (m, 15H).

Example 10

Preparation of Compound C

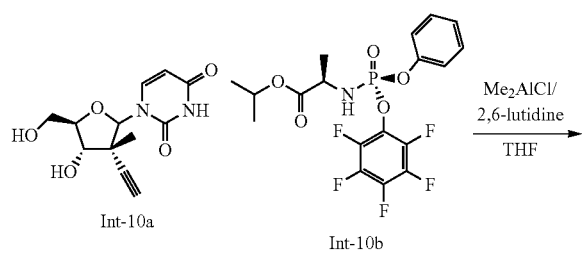

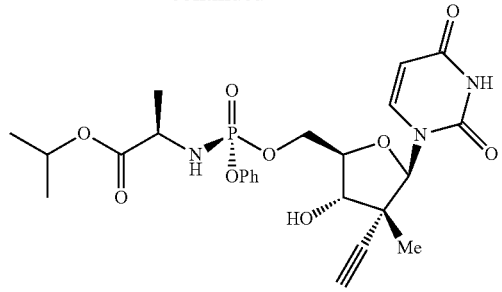

Compound C

Compound Int-10a (10 g, 32.7 mmol, made using the methods described in International Publication No. WO 2012/142085) was dissolved in methanol (60 mL, 6 volumes) and the resulting solution was filtered and solvent switched to tetrahydrofuran (THF, 150 mL, 15 Volumes). To the resulting solution was added compound Int-10b (17.79 g, 39.3 mmol, 1.2 equivalents, made using the methods described in International Publication No. WO 2013/177219) followed addition of Me$_2$AlCl (16.68 mL, 1M in hexanes, 16.68 mmol, 0.51 equivalents) over 2 hours. To the resulting mixture was added 2,6-lutidine (3.81 mL, 32.7 mmol, 1 equivalent), and the resulting reaction was allowed to age at room temperature for about 15 hours. After this time the reaction mixture was heated at 40° C. and allowed to stir at this temperature for 2 hours. The reaction mixture was then cooled to 20° C., IPAc (100 mL, 20 volumes) was added and to the resulting solution was added 2M HCl (50 mL, 10 volumes). The resulting mixture was transferred to a separatory funnel and the organic layer was collected was washed sequentially with 2M HCl (25 mL, 5 volumes), water (35 mL, 7 volumes), then water (60 mL, 12 volumes). The organic phase was then solvent switched to IPAc (final solution volume was 80 mL) and seeded with compound C. The resulting suspension was filtered and washed with IPAc to provide compound C as a white solid, 13.15 g, 75%. $^1$H NMR (400 MHz, DMSO), 11.05, (s, 1H); 7.56, (d, J=8.01 Hz, 1H); 7.38, (t, J=7.99 Hz, 2H); 7.25, (d, J=8.01 Hz, 2H); 7.18 (t, 7.61 Hz, 1H); 6.15 (dd, J=10.01 & 12.97 Hz, 1H); 6.09, (s, 1H), 5.94 (d, J=5.2 Hz, 1H); 5.54, (dd, J=7.91 & 2.00 Hz, 1H); 4.85, (m, 1H); 4.35, (m, 1H), 4.26, (m, 1H); 4.02, (m, 1H), 3.77, (m, 1H); 3.68, (m, 1H); 3.34, (s, 1H); 1.22, (d, J=6.81 Hz, 3H); 1.15, (d, 6.81 Hz, 3H); 1.13 (d, 6.81 Hz, 3H); 1.06 (s, 3H).

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A process for making a compound of formula (II):

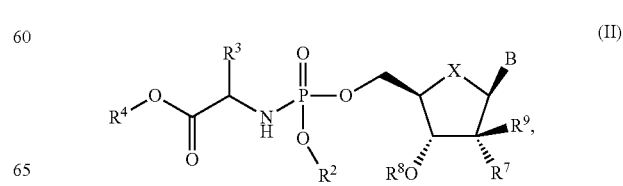

wherein said process comprising the step of contacting a compound of formula (I):

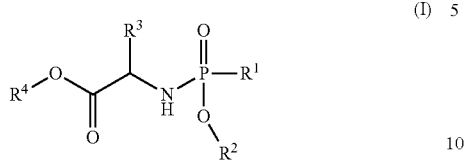

with a compound of formula (III):

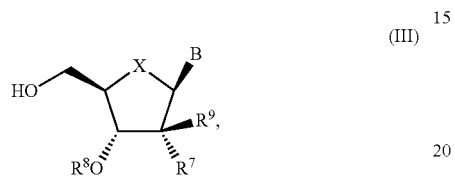

in the presence of an aluminum complex having the formula the formula $(C_1\text{-}C_6 \text{ alkyl})_2\text{AlCl}$ or $\text{Al}(\text{—O—}(C_1\text{-}C_6 \text{ alkyl}))_3$, and base 2,6-lutidine, in an organic solvent A for a time and at a temperature sufficient to form the compound of formula (II), wherein:

X is O, S or $CH_2$;

B is a natural or non-natural purine or pyrimidine base, or B is selected from one of the following groups:

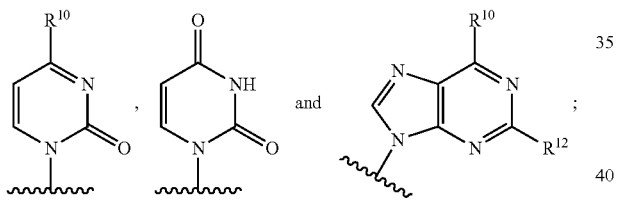

$R^1$ is selected from the group consisting of pentafluorophenyl, and 3-chloropyridyl;

$R^2$ is selected from the group consisting of $C_6\text{-}C_{10}$ aryl, 5 or 6-membered monocyclic heteroaryl and 9 or 10-membered bicyclic heteroaryl, wherein said $C_6\text{-}C_{10}$ aryl group, said 5 or 6-membered monocyclic heteroaryl group and said 9 or 10-membered bicyclic heteroaryl group can be optionally substituted with one or more $R^5$ groups;

$R^3$ is selected from the group consisting of $C_1\text{-}C_6$ alkyl, $C_3\text{-}C_7$ cycloalkyl, phenyl or benzyl, wherein said $C_3\text{-}C_7$ cycloalkyl group, said phenyl group and the phenyl moiety of said benzyl group can be optionally substituted with one or more $R^5$ groups;

$R^4$ is selected from the group consisting of $C_1\text{-}C_6$ alkyl, $C_2\text{-}C_6$ alkenyl, $—(C_1\text{-}C_3 \text{ alkylene})_m\text{-}(C_3\text{-}C_{14} \text{ cycloalkyl})$ and $—(C_1\text{-}C_3 \text{ alkylene})_m\text{-}(C_6\text{-}C_{10} \text{ aryl})$;

each occurrence of $R^5$ is independently selected from the group consisting of $—C_1\text{-}C_6$ alkyl, halo, $—OR^6$, $—C(O)R^6$, $—CO_2R^6$, $—SR^6$, $—C_1\text{-}C_6$ hydroxyalkyl, $—C_1\text{-}C_6$ haloalkyl, $—N(R^6)_2$, $—S(O)R^6$, $—S(O)_2R^6$, $—CN$ and $—NO_2$;

each occurrence of $R^6$ is independently selected from the group consisting of H, $C_1\text{-}C_6$ alkyl, $C_1\text{-}C_6$ haloalkyl, $C_1\text{-}C_6$ hydroxyalkyl, $—(C_1\text{-}C_3$ alkylene$)_m\text{-}(C_3\text{-}C_7$ cycloalkyl$)$, $—(C_1\text{-}C_3$ alkylene$)_m\text{-}(C_6\text{-}C_{10}$ aryl$)$, $—(C_1\text{-}C_3$ alkylene$)_m\text{-}(4$ to 7-membered heterocycloalkyl$)$, $—(C_1\text{-}C_3$ alkylene$)_m\text{-}(5$- or 6-membered monocyclic heteroaryl$)$ or $—(C_1\text{-}C_3$ alkylene$)_m\text{-}(9$- or 10-membered bicyclic heteroaryl$)$;

$R^7$ is selected from the group consisting of H, $C_1\text{-}C_6$ alkyl, $C_2\text{-}C_6$ alkenyl, $C_2\text{-}C_6$ alkynyl, F, $—CN$, $—N_3$, $—N(R^9)_2$, $C_1\text{-}C_6$ haloalkyl, $C_1\text{-}C_6$ hydroxyalkyl, $C_2\text{-}C_6$ alkenyl, $C_2\text{-}C_6$ alkynyl and $C_3\text{-}C_7$ cycloalkyl;

$R^8$ is selected from the group consisting of H and $—C(O)R^{13}$;

each occurrence of $R^9$ is independently selected from the group consisting of H, $C_1\text{-}C_6$ alkyl, $C_6\text{-}C_{10}$ aryl and $C_3\text{-}C_7$ cycloalkyl;

$R^{10}$, $R^{11}$ and $R^{12}$ are each independently selected from the group consisting of H, $C_1\text{-}C_6$ alkyl, $C_2\text{-}C_6$ alkenyl, $C_2\text{-}C_6$ alkynyl, $C_3\text{-}C_7$ cycloalkyl, halo, $—OR^{14}$, $—SR^{14}$, $—S(O)R^{14}$, $—S(O)_2R^{14}$, $—S(O)_2N(R^{14})_2$, $—NHC(O)OR^{14}$, $—NHC(O)N(R^{14})_2$, $C_1\text{-}C_6$ haloalkyl, $C_1\text{-}C_6$ hydroxyalkyl, $—O—(C_1\text{-}C_6$ haloalkyl$)$, $—CN$, $—NO_2$, $—N(R^{14})_2$, $—NH(C_1\text{-}C_6$ alkylene$)$-(5- or 6-membered monocyclic heteroaryl), $—NH(C_1\text{-}C_6$ alkylene$)$-(9- or 10-membered bicyclic heteroaryl), $—C(O)R^{14}$, $—C(O)OR^{14}$, $—C(O)N(R^{14})_2$ and $—NHC(O)R^{14}$;

each occurrence of $R^{13}$ is independently H or $C_1\text{-}C_6$ alkyl;

each occurrence of $R^{14}$ is independently selected from the group consisting of H, $C_1\text{-}C_{10}$ alkyl, $C_1\text{-}C_6$ haloalkyl, $C_1\text{-}C_6$ hydroxyalkyl, $—(C_1\text{-}C_3$ alkylene$)_m\text{-}(C_3\text{-}C_7$ cycloalkyl$)$, $—(C_1\text{-}C_3$ alkylene$)_m\text{-}(C_6\text{-}C_{10}$ aryl$)$, $—(C_1\text{-}C_3$ alkylene$)_m\text{-}(4$ to 7-membered heterocycloalkyl$)$, $—(C_1\text{-}C_3$ alkylene$)_m\text{-}(5$- or 6-membered monocyclic heteroaryl) and $—(C_1\text{-}C_3$ alkylene$)_m\text{-}(9$- or 10-membered bicyclic heteroaryl); and each occurrence of m is independently 0 or 1.

2. The process of claim 1, wherein the aluminum complex is $(CH_3)_2\text{AlCl}$ or $\text{Al}(t\text{-BuO})_3$.

3. The process of claim 1, wherein the compound of formula (I) is:

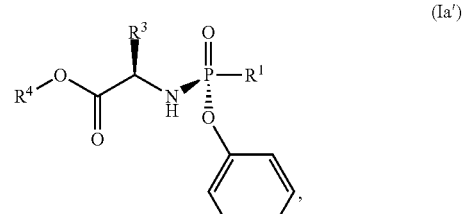

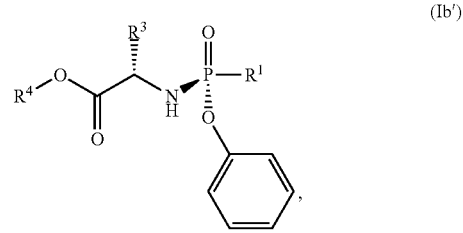

-continued

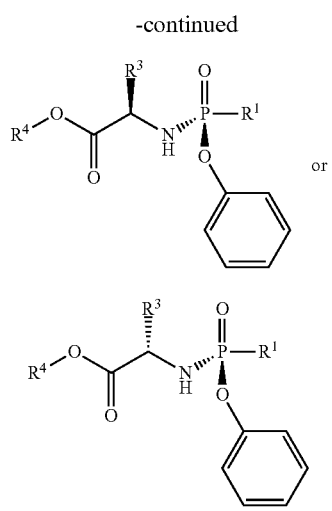

wherein:
R¹ is pentafluorophenyl or 3-chloropyridyl;
R³ is —C₁-C₆ alkyl; and
R⁴ is —C₁-C₆ alkyl.

4. The process of claim 3, wherein R¹ is pentafluorophenyl.

5. The process of claim 3, wherein the compound of formula (I) is:

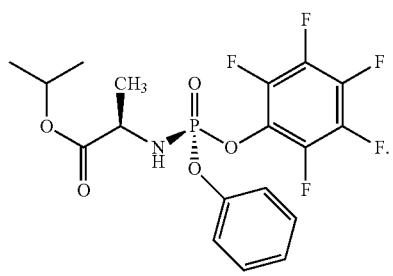 [SMILES: CC(C)OC(=O)[C@@H](C)N[P@](=O)(Oc1ccccc1)Oc1c(F)c(F)c(F)c(F)c1F]

6. The process of claim 1, wherein organic solvent A is THF.

7. The process of claim 1, wherein the compound of formula (III) has the formula (IIIa):

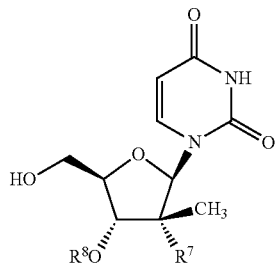

wherein R⁷ is selected from the group consisting of F, —CN, C₂-C₆ alkynyl, —NH₂ and —N₃; and R⁸ is H or —C(O)CH(CH₃)₂.

8. The process of claim 7, wherein R⁷ is F, —C≡CH, —N₃ or —NH₂; and R⁸ is H.

9. The process of claim 7, wherein R⁷ —CN and R⁸ is —C(O)CH(CH₃)₂.

10. The process of claim 1, wherein the compound of formula (II) that is made is selected from the group consisting of:

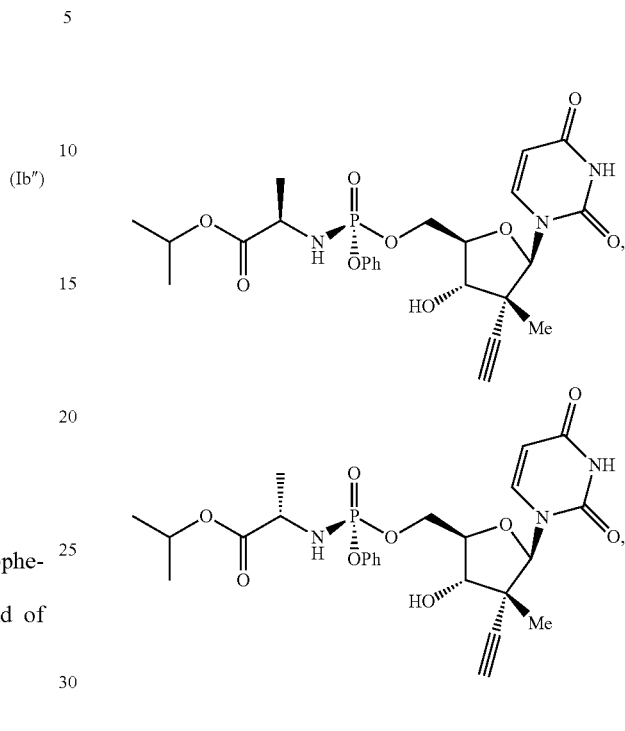

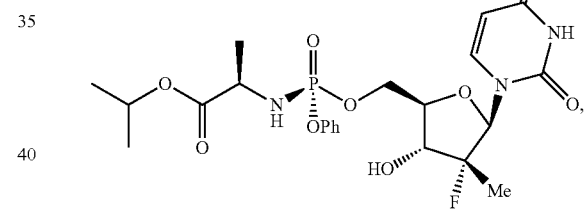

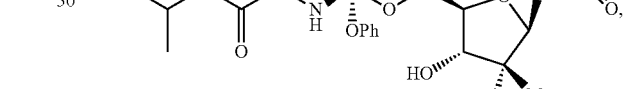

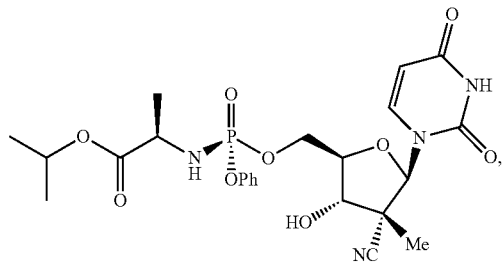

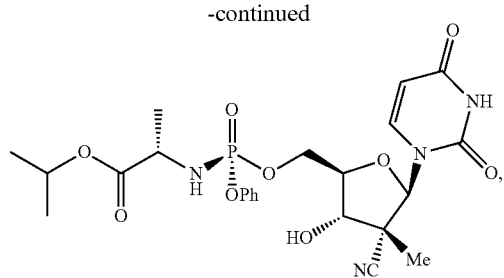
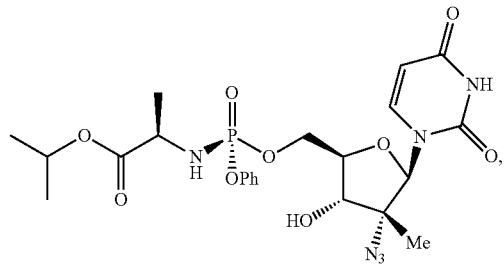
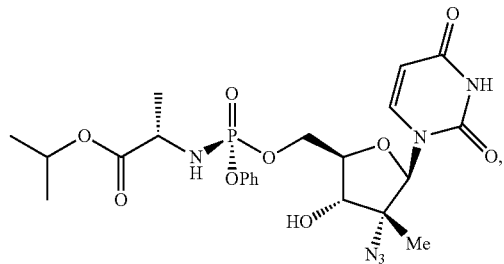
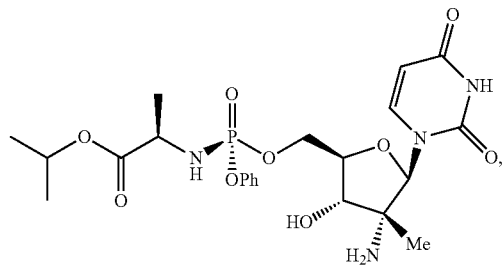
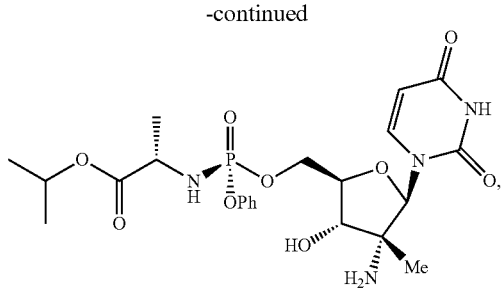
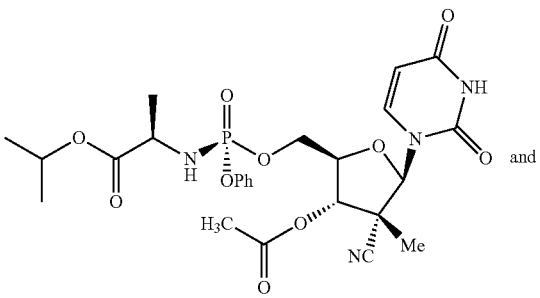
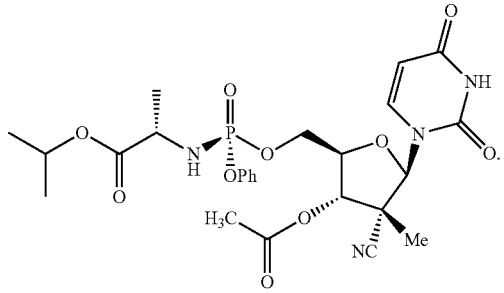
or a pharmaceutically acceptable salt thereof.
* * * * *